United States Patent [19]
Segi et al.

[11] Patent Number: 5,955,631
[45] Date of Patent: Sep. 21, 1999

[54] METHOD FOR INDUSTRIAL PURIFICATION OF CAPSAICIN

[75] Inventors: Hisashi Segi; Shuji Yamada; Satoshi Kato; Shoji Murasugi, all of Gifu-ken, Japan

[73] Assignee: Alps Pharmaceutical Ind. Co., Ltd., Gifu-ken, Japan

[21] Appl. No.: 09/116,453

[22] Filed: Jul. 16, 1998

[30] Foreign Application Priority Data

Jul. 18, 1997 [JP] Japan ..................................... 9-193760

[51] Int. Cl.[6] ................................................. C07C 209/84
[52] U.S. Cl. ............................................ 564/206; 564/207
[58] Field of Search ...................... 564/206, 207

[56] References Cited

PUBLICATIONS

Wall, Peter. Argentation HPTLC as an Effective Separation echnique for the cis/trans Isomers of Capsaicin. J. Planar Chromatog. 10(1) pp. 4–9, 1987.

Constant, Howard L., et al., Journal of Natural Products, vol. 58, No. 12, pp. 1925–1928 (Dec. 1995).

Suzuki, T., et al., Journal of Chromatography, 198, 217–223 (1980).

*Primary Examiner*—Brian M. Burn

[57] ABSTRACT

The invention provides a method for industrial purification of Capsaicin in high purity from capsinoids (Capsaicin and analogues), more specifically, a method for industrial purification of Capsaicin which comprises contacting capsinoids containing Capsaicin in a hydrophilic solvent with a silver compound in an aqueous solution to form a Capsaicin-silver complex which is soluble in water, and recovering highly pure Capsaicin from the Capsaicin-silver complex without chromatography.

4 Claims, 1 Drawing Sheet

METHOD FOR INDUSTRIAL PURIFICATION OF CAPSAICIN

The invention relates to a method for industrial purification of Capsaicin in a high purity from capsinoids, which consist of Capsaicin and its analogues.

BACKGROUND OF THE INVENTION

Capsaicin is included in fruits of Capsium annuum Linne or its variety, solanaceae, in an amount of about 0.2% by weight of the fruits. Capsium annuum is adopted in the Pharmacopeia of Japan and when a tincture or a solution of Capsaicin is put on certain area of skin, mucous membrane or a dog's ear, blood vessels of the area are expanded and the area is congested. Capsaicin, a main component of Capsium annuum, appears to have strong and stimulative effectiveness on receptors of circulatory and respiratory reflex. In experiments of internal organs removed from humans or experimental animals, a tincture of Capsium annuum or Capsaicin promotes digestion and its small amount promotes salivary and gastric secretion, however its large amount suppresses the salivary and gastric secretion. The tincture of Capsium annuum is used as a local stimulant and may be incorporated in external remedies such as plasters, solutions or ointments.

So-called capsaicin on the market, referred to hereinafter as commercial capsaicin, includes capsinoids of the following chemical structures, (1) Capsaicin (60 to 65% by weight), (2) Nordihydrocapsaicin, (3) Nonylvanillylamide, (4) Dihydrocapsaicin, (5) Decanylvanillylamide and (6) Homocapsaicin. A total amount of capsinoids in the commercial capsaicin is more than 95% by weight and a main component of the commercial capsaicin, Capsaicin, is about 60 to about 65% by weight.

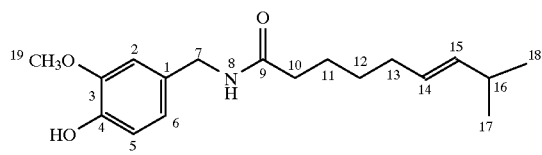

(1) Capsaicin ($C_{18}H_{27}NO_3$) M.W. 305

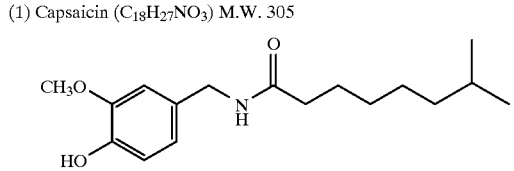

(2) Nordihydrocapsaicin ($C_{17}H_{27}NO_3$) M.W. 293

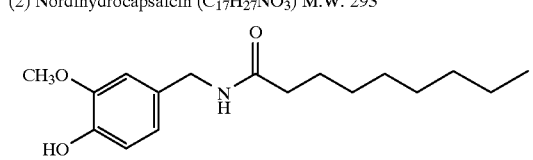

(3) Nonylvanillylamide ($C_{17}H_{27}NO_3$) M.W. 293

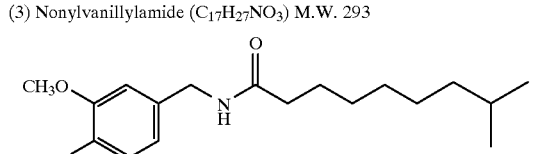

(4) Dihydrocapsaicin ($C_{18}H_{29}NO_3$) M.W. 307

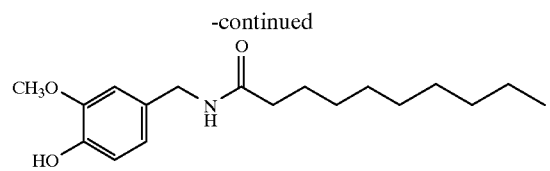

(5) Decanylvanillylamide ($C_{18}H_{29}NO_3$) M.W. 307

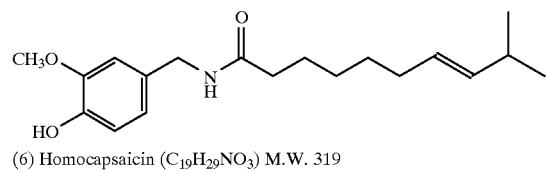

(6) Homocapsaicin ($C_{19}H_{29}NO_3$) M.W. 319

Capsaicin have been conventionally isolated and purified by repeatedly subjecting crude capsaicin to several kinds of a large column (ODS, Phenyl, silica gel, etc.) of high performance liquid chromatography.

For example, 30 g of commercial capsaicin (60 to 65% by weight as a purity of Capsaicin) is dissolved in 300 ml of 70% methanol. The resulting solution is treated to decolor by stirring with 3 g of activated charcoal 1 hour and filtered to give a solid. The solid is dissolved in 300 ml of 70% alcohol to give a sample solution in a final concentration of 10% by weight of the solid. The sample solution is subjected to ODS column (10 cm in diameter and 50 cm in length) of high performance liquid chromatography (HPLC) to obtain fractions. Fractions including predominantly Capsaicin are collected and concentrated to give about 15 g as solid. Using the solid, 300 ml of aqueous 70% alcohol solution in a final concentration of 5% by weight of the solid is prepared and the aqueous alcohol is subjected a Phenyl column (20 cm in diameter and 100 cm in length). Fractions including predominantly Capsaicin are collected and concentrated to give a residue. The residue is dissolved in an alkaline solution, and then acetic acid is added thereto and precipitate. The obtained crystals are rinsed and dried to give 5.4 g of Capsaicin in a purity of more than 98% by weight and an yield based on commercial capsaicin is 18% by weight.

While in order to isolate Nordihydrocapsaicin having a peak near to Capsaicin's peak in HPLC and column chromatography, a method for qualitative and quantitative analysis of Capsaicin is known which comprises previously forming a silver complex and then subjecting to HPLC or column chromatography. However, the method is directed to qualitative and quantitative analysis and uses column chromatography.

And therefore, a method directed to an industrial purification without subjecting to chromatography has not been known as a method for preparing. Capsaicin in a high purity in a large scale.

According to a conventional method for purification of Capsaicin, it is difficult to remove impurities such as Nordihdrocapsaicin, Vanylamide nonylate and the like which are analogous to Capsaicin. In addition, since an amount of Capsaicin obtained by one purification procedure is severe gram order and it also depends on an amount of column-loading, usually, the column-loading amount is small, therefore, in order to obtain a large amount of Capsaicin, it is necessary to repeat the purification procedure or enlarge a column scale. Therefore, there is a limitation in the purification of Capsaicin in industrial scale and also it takes long time to obtain Capsaicin in a large quantity.

SUMMARY OF THE INVENTION

The object of the invention is to remove drawbacks as described above and to provide a method for purification of Capsaicin in high purity, which is expensive and used as a raw material of a medicinal drug, by purifying promptly and also in large quantity.

The present invention provides a method for industrial purification of Capsaicin which comprises contacting capsinoids containing Capsaicin in a hydrophilic solvent with a silver compound in an aqueous solution to form a Capsaicin-silver complex which is soluble in water and recovering highly pure Capsaicin from the Capsaicin-silver complex without chromatography.

Capsaicin hardly soluble in water is transformed into a water-soluble Capsaicin-silver complex by contacting an aqueous solution of capsinoids including capsaicin with a silver compound in an aqueous solution. Capsaicin in high purity may be obtained by contacting the resultant solution with a hydophobic solvent which is capable of dissolving the Capsaicin-silver complex to extract the Capsaicin-silver complex. According to the method, a large quantity of Capsaicin in high purity can be obtained at one operation procedure.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
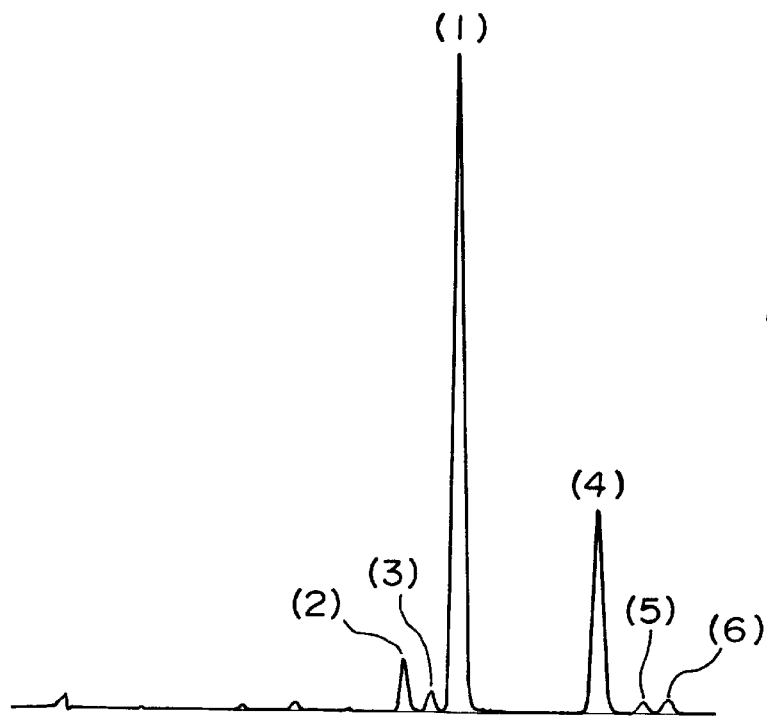
FIG. 1 shows a HPLC chart of commercial capsaicin.
Figure 2:
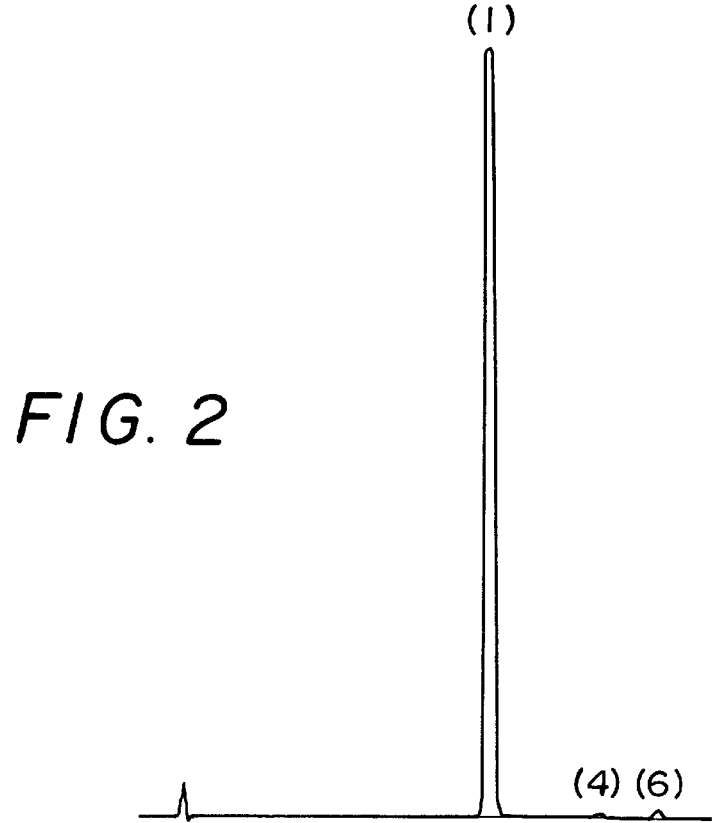
FIG. 2 shows purified capsaicin obtained by the method of the present invention.

(1) . . . Capsaicin, (2) . . . Nordihydrocapsaicin, (3) . . . Nonylvanillylamide, (4) . . . Dihydrocapsaicin (5) . . . Decanylvanillylamide (6) . . . Homocapsaicin

DETAILED DESCRIPTION OF PREFERRED EMBODIMENTS

A purification process of the invention is characterized that after contacting capsinoids containing Capsaicin in a hydrophilic solvent with a silver compound in an aqueous solution to form a Capsaicin-silver complex, an aqueous layer including the Capsaicin-silver complex is extracted with a hydrophobic solvent which hardly dissolves the Capsaicin-silver complex, and then with a hydrophobic solvent which is capable of dissolving the capsaicin-silver complex, the resultant hydrophobic solvent including the Capsaicin-silver complex is treated by an aqueous acidic solution to obtain Capsaicin in high purity.

More specifically, 1 part by weight of Capsaicin in capsinoids dissolved in a hydrophilic solvent is contacted with an aqueous solution of 3 to 20 parts by weight of a silver nitrate. According to the method of the present invention, for example, the main component, Capsaicin (60 to 65% by weight), may be isolated and purified from commercial capsaicin including 95% by weight of total capsinoids (i.e. the components of capsinoids are Capsaicin, Nordihydrocapsaicin, Nonylvanillylamide, Dihydrocapsaicin, Decanylvanillylamide, Homocapsaicin, etc.). Purified Capsaicin may be used as a starting material of a medicinal drug, for example, analgestic.

PREFERRED EMBODIMENTS OF THE INVENTION

The term "capsinoid" means Capsaicin or its analogues. Specific examples of the analogues are Nordihydrocapsaicin, Nonylvanillylamide, Dihydrocapsaicin, Decanylvanillylamide, Homocapsaicin, etc.

The hydrophilic solvent herein may be any hydrophilic solvent which is capable of dissolving Capsaicin, and it may be acetone, methanol, ethanol, isopropyl alcohol, preferably, acetone.

The amount of the hydrophilic solvent relation to capsinoids is not limited, preferably, 0.25 to 2 parts by weight for 1 part by weight of capsinoids, more preferably 0.5 to 1.5 parts by weight.

The silver compound to form a Capsaicin-silver complex may include silver nitrate, silver chlorate, silver perchlorate, silver acetate and silver sulfate, preferably silver nitrate. For simplification of description, silver nitrate is used hereafter as the silver compound.

Silver nitrate in relation to 1 part by weight of Capsaicin is 3 to 20 parts by weight, preferably 4 to 10 parts by weight, more preferably 5 to 7 parts by weight, the most preferably about 6 parts by weight.

Commercial capsaicin, includes 60 to 65% by weight of Capsaicin, and therefore, based on commercial capsaicin, silver nitrate per 1 part by weight of commercial capsaicin is 2 to 12 parts by weight.

Concentration of a silver nitrate solution is preferably 60 to 90% (w/v), more preferably 70 to 80% (w/v), the most preferably about 75% (w/v).

The hydrophilic solution with capsinoids is contacted the silver nitrate solution preferably at 5 to 60° C., more preferably 10 to 40° C., most preferably 15 to 25° C., preferably at pH 6 to 10, more preferably pH 6 to 8, most preferably pH 7.5. A period for contact of the capsinoids with silver nitrate may be any period in which Capsaicin-silver complex can be formed, and therefore, is not limited. The Capsaicin-silver complex may be formed 1 to 4 hours.

As a hydrophobic solvent which can hardly dissolves Capsaicin, hexane, petroleum ether, petroleum benzin and the like may be exemplified.

A hydrophobic solvent which is capable of dissolving Capsaicin includes methylene chloride, ether, isopropyl alcohol, ethyl acetate, chloroform and the like, preferably methylene chloride.

Examples of an acid in the acidic solution includes hydrochloric acid, nitric acid, acetic acid, sulfuric acid, phosphoric acid, preferably hydrochloric acid. Concentration of the acidic solution may be about 1 N.

"high purity" herein means a purity of more than 98% by weight.

A process for purification of the present invention is illustrated as follows;

Capsinoids (for example, commercial capsaicin includes 60 to 65% by weight of Capsaicin) are dissolved into the same amount of a hydrophilic solvent which is capable of dissolving Capsaicin (for example, acetone), and mixed with a solution of silver nitrate which has been previously prepared (for example, silver nitrate is dissolved in water of 4 to 6 times as much as weight of commercial capsaicin) under stirring for 1 to 4 hours (Formation of a Capsaicin-silver complex). Stirring is stopped and the solution is allowed to stand to form two layers, an upper layer of a water insoluble part and a lower layer of a water soluble part.

The lower layer of the water soluble part is treated to remove fat with a hydrophobic solvent which can hardly dissolve the Capsaicin-silver complex, for example, hexane, followed by shaking with a solvent (0.1 volume to a volume equivalent of the lower layer) which can dissolve Capsaicin-silver complex, for example, methylene chloride. The methylene chloride organic layer is separated. Incidentally, Capsaicin has partly liberated from the Capsaicin-silver complex at this stage.

The organic layer is shaken with an acidic solution of about 1 N (for example, a hydrochloric acid solution), further with a sodium chloride saturated solution to remove acid. The organic layer is concentrated to give a residue which is repeatedly recrystallized from toluene, xylene, acetonitrile, diethylene glycol, pyridine, ether, isopropyl ether or the like, preferably toluene and/or xylene. The recrystallization is repeatedly 1 to 5 times, preferably 3 times to filter off crystals, Capsaicin in high purity.

Capsaicin in a high purity $C_{18}H_{27}NO_3$ (MW: 305)

Property: white needle crystals

M.P.: 65.5° C.

Purity: more than 98% by weight

Conditions of HPLC

Measured Wavelength: 280 nm

Columns Phenyl (5 $\mu$: 4.6×250 mm)

Temperature: 40° C.

Eluent: acetonitrile—aqueous 0.1% phosphoric acid solution (=37 : 63)

Current velocity: 1.0 ml/min.

The purity of Casaicin and Capinoids herein were measured under the conditions of HPLC as described above.

IR(KBr) $\gamma cm^{-1}$: 3320(OH), 2960(CH), 1690(C=O), 1610(arom C=C)

UV $\lambda$ max nm(log $\epsilon$): (MeOH)227(3.91), 280(3.43)

1H-NMR(CDCl$_3$): 0.94(6H, d, J=6.8 Hz, 17, 18-H), 1.26–1.75(4H, m, 11, 12-H), 1.82–2.01(2H, m, 13-H), 2.20 (2H, t, J=7.5 Hz, 10-H), 2.09–2.28(1H, m, 16-H), 3.87(3H, a, OCH$_3$), 4.35(2H, d, J=5.5 Hz, 7-H), 5.35(2H, m, 14, 15-H), 5.65(2H, br s, NH, OH), 6.76(1H, dd, J=7.7 Hz, 2.2 Hz, H-6), 6.81(1H, d, J=2.2 Hz, H-2), 6.89(1H, d, J=7.7 Hz, H-5) $^{13}$C-NMR(CDCl$_3$): 22.7(C-17, C-18), 25.3(C-11), 29.3 (C-12), 31.0(C-16), 32.2(C-13), 36.7(C-10), 43.6(C-7), 56.0 (C-19), 110.9(C-2), 114.6(C-5), 120.9(C-6), 126.6(C-14), 130.5(C-1), 138.2(C-15), 145.4(C-4), 146.9(C-3), 172.9(C-9)

EXAMPLES

Example 1

Commercial capsaicin including 63.5% by weight of Capsaicin (476.5 g as Capsaicin), 750 g was dissolved into the same amount of acetone followed by mixing a solution of silver nitrate previously prepared (2900 g of silver nitrate was dissolved in 3900 ml of water) under stirring pH 7.5 at 19° C. for 3 hours to form a Capsaicin-silver complex. Stirring was stopped and the solution was allowed to stand and then a water layer (about 5 L) was separated. Hexane (about 5 L) was added to the water layer followed by shaking. The water layer was again separated and 2.5 mL of dichloromethane was added thereto followed by shaking to separate a dichloromethane layer (i). Again to the water layer, 1.25 mL of dicbloromethane was added followed by shaking to separate a dichloromethane layer (ii). Two dichloro-methane layers (i) and (ii) are collected together and concentrated to a volume of 1.25 L. To the dichloromethane layer, 1.25 mL of 1 N hydrochloric acid solution was added followed by shaking, this procedure was repeated three times and finally 1.25 mL of saturated sodium chloride solution was added to the dichloromethane layer followed by shaking. The dichloromethane solution was concentrated to give a residue, which was two times recrystallized from 1 L of xylene, and crystals were filtered off.

The crystals were dried to give 150 g of capsaicin in high purity (more than 98%), and an yield is 20% based on commercial capsaicin.

Example 2

Commercial capsaicin including 63.5% by weight of Capsaicin (476.5 g as Capsaicin), 750 g was dissolved into the same amount of isopropyl alcohol and mixed with a solution of silver nitrate previously prepared (2900 g of silver nitrate was dissolved in 3900 ml of water) under stirring pH 7.5 at 18° C. for 2.5 hours to form Capsaicin-silver complex. Stirring was stopped and the solution was allowed to stand and then a lower water layer (about 5 L) was separated. Petroleum ether (about 5 L) was added to the water layer followed by shaking. The water layer was again separated and 2.5 mL of isopropyl alcohol was added thereto followed by shaking and an isopropyl ether layer (i) was separated. Again to the water layer, 1.25 mL of isopropyl ether was added followed by shaking and an isopropyl ether layer (ii) was separated. Two isopropyl ether layers (i) and (ii) are collected together and concentrated to a volume of 1.25 L. To the isopropyl ether layer, 1.25 mL of 1 N phosphoric acid solution was added followed by shaking, this procedure was repeated three times, and finally 1.25 mL of excessively saturated sodium chloride solution was added thereto followed by shaking. The isopropyl ether layer was concentrated to give a residue, which was recrystallized from 1 L of xylene and crystals were filtered off. The crystals were precipitated from toluene followed by drying to give 135 g of dried Capsaicin of high purity (more than 98%) and an yield is 18% based-on commercial capsaicin.

Example 3

Commercial capsaicin including 60 to 65% by weight of Capsaicin (476.5 g as Capsaicin), 750 g was dissolved into the same amount of methanol followed by mixing a solution of silver nitrate previously prepared (6400 g of silver nitrate was dissolved in 30 L of water) to contact under stirring at pH 7.5 at 20° C. for 3 hours to form a Capsaicin-silver complex. Stirring was stopped and the solution was allowed to stand and then a lower water layer (about 29 L) was separated. Hexane 10 L was added to the water layer followed by shaking. The water layer was again separated and 5 L of dichloromethane was added thereto followed by shaking and a dichloromethane layer (i) was separated. Again to the water layer, 1.25 mL of dichloromethane was added followed by shaking and a dichloromethane layer (ii) was separated. Two dichloromethane layers (i) and (ii) are collected together and concentrated to 1 L. To the dichloromethane layer, 1 L of 1 N nitric acid solution was added followed by shaking and finally 0.8 L of saturated sodium chloride solution was added thereto followed by shaking. The dichloromethane layer was concentrated to give a residue, which was two times recrystallized from 500 mL of toluene and crystals were filtered off. The crystals were dried to give 113 g of Capsaicin in high purity (more than 98%), and an yield is 15% based on commercial capsaicin.

The invention being thus described, it will be obvious that the same may be varied in many ways. Such variations are not to be regarded as a departure from the spirit and scope of the invention, and all such modifications as would be obvious to one those skilled in the art are intended to be included within scope of the following claims.

What is claimed is:

1. A method for industrial purification of Capsaicin which comprises contacting capsinoids containing Capsaicin in a hydrophilic solvent with a silver compound in an aqueous solution to form a Capsaicin-silver complex which is soluble in water and recovering highly pure Capsaicin from the Capsacin-silver complex without chromatography.

2. A method for industrial purification of Capsaicin which comprises contacting capsinoids containing Capsaicin in a hydrophilic solvent with a silver compound in an aqueous solution to form a Capsaicin-silver-complex which is soluble in water to separate a water layer including the Capsaicin-silver complex, followed by treating the water layer including a Capsaicin-silver complex with a hydrophobic solvent which hardly dissolves the Capsaicin-silver complex, treating again the water layer with another hydrophobic solvent which is capable of the Capsaicin-silver complex to form a solution and treating the formed solution with acidic solution to give Capsaicin in high purity.

3. A method for industrial purification of Capsaicin which comprises contacting capsinoids containing a Capsaicin in a hydrophilic solvent with 3 to 20 parts by weight of a silver compound in relation to 1 part by weight of Capsaicin in an aqueous solution to form a Capsaicin-silver complex which is soluble in water, separating a water layer including the Capsaicin-silver complex, followed by treating the water layer including the Capsaicin-silver complex with a hydrophobic solvent which hardly dissolves the Capsaicin-silver complex, treating again the water layer with another hydrophobic solvent which is capable of dissolving the Capsaicin-silver complex to form a solution and treating the formed solution with acidic solution to give Capsaicin in high purity.

4. A method for industrial purification of Capsaicin which comprises contacting commercial capsaicin containing 60 to 65% by weight of Capsaicin in a hydrophilic solvent with 2 to 12 parts by weight of a silver compound in relation to 1 part by weight of commercial capsaicin in an aqueous solution to form a Capsaicin-silver complex which is soluble in water to separate a water layer including the Capsaicin-silver complex, followed by treating the water layer including the Capsaicin-silver complex with a hydrophobic solvent which hardly dissolves the Capsaicin-silver complex, treating again the water layer with another hydrophobic solvent which is capable of dissolving the Capsaicin-silver complex to form a solution, and treating the formed solution with acidic solution to give capsaicin in high purity.

* * * * *